United States Patent [19]

Birbara et al.

[11] Patent Number: 5,104,810
[45] Date of Patent: Apr. 14, 1992

[54] ZERO GRAVITY PURGE AND TRAP FOR MONITORING VOLATILE ORGANIC COMPOUNDS

[75] Inventors: Philip J. Birbara, Windsor Locks; Timothy A. Nalette, Tolland; John W. Steele, Torrington, all of Conn.

[73] Assignee: United Technologies Corporation, Hartford, Conn.

[21] Appl. No.: 544,763

[22] Filed: Jun. 27, 1990

[51] Int. Cl.⁵ .............................................. H01N 21/00
[52] U.S. Cl. .................................. 436/161; 436/178; 436/146; 436/160; 422/89; 422/93; 73/23.41; 585/818
[58] Field of Search .................... 422/89, 93; 436/177, 436/178, 139, 140, 141, 158, 160, 161, 162, 145, 146; 73/23.41, 61.1 C; 585/818

[56] References Cited

U.S. PATENT DOCUMENTS

| | | | |
|---|---|---|---|
| 4,500,432 | 2/1985 | Poole et al. | 210/659 |
| 4,715,217 | 2/1987 | Coyne et al. | 73/61.1 C |
| 4,745,237 | 5/1988 | Ballard et al. | 570/176 |
| 4,952,751 | 8/1990 | Blume et al. | 585/818 |

OTHER PUBLICATIONS

"Amberlite ®/Duolite ® Ion Exchange Resins", Technical Notes, Rohm & Haas Co.

Primary Examiner—Robert J. Hill, Jr.
Assistant Examiner—Abanti B. Singla
Attorney, Agent, or Firm—Alan Cohen; Pamela J. Mercier

[57] ABSTRACT

Traditionally, volatile organic compounds are monitored using the purge and trap technique required by the U.S. Environmental Protection Agency. However, this technique operates in two phases, liquid and gas, requiring gravity to effect the separation of the two phases. The present invention, which can be automated, incorporates a microporous hydrophobic bladder to permit zero gravity monitoring of volatile organic compounds in an aqueous solution.

12 Claims, 1 Drawing Sheet

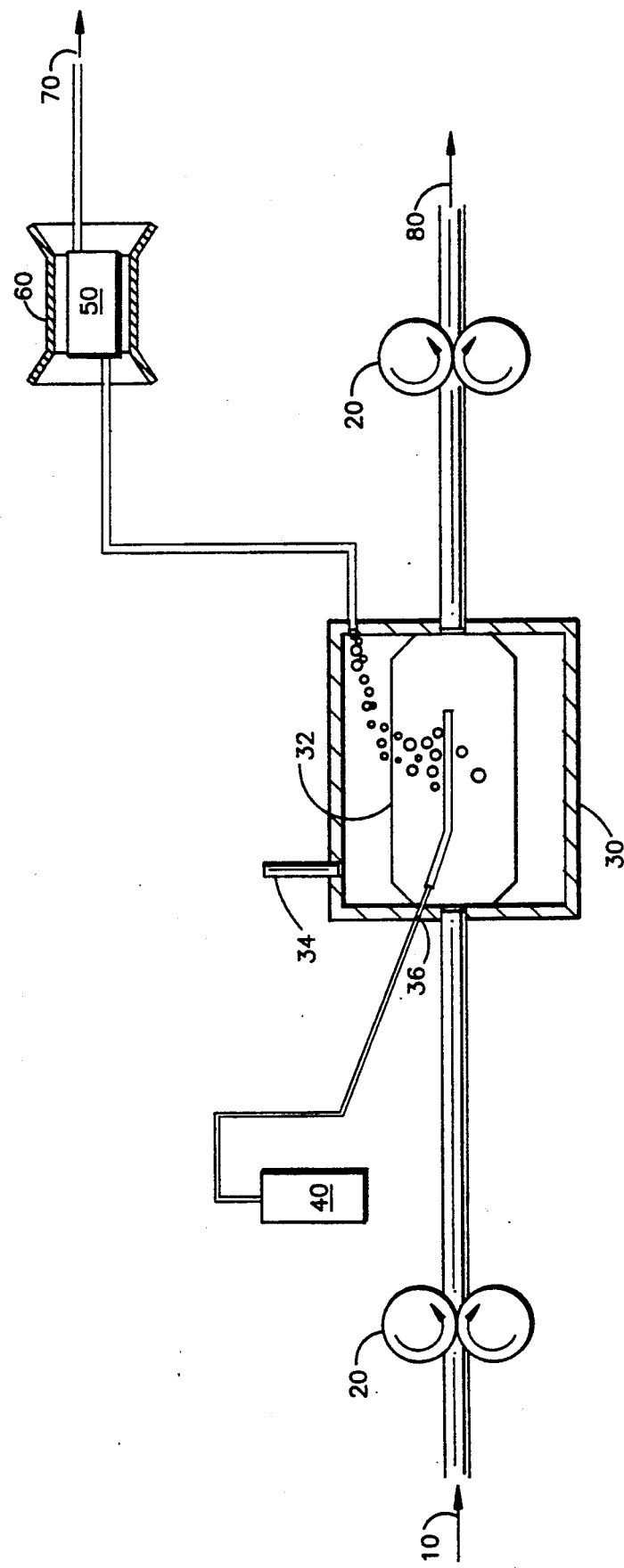

ZERO GRAVITY PURGE AND TRAP FOR MONITORING VOLATILE ORGANIC COMPOUNDS

CROSS REFERENCE

This application relates to copending, U.S. patent application Ser. No. 07/544,766, for TOTAL ORGANIC HALOGEN ANALYZER, filed on June 27, 1990 U.S. patent application Ser. No. 07/544,764, for AUTOMATED BIOLUMINESCENCE MICROBIAL MONITOR, filed June 27, 1990; U.S. patent application Ser. No. 07/544,767, for ZERO GRAVITY COMPATIBLE TOTAL ORGANIC AND INORGANIC CARBON ANALYZER, filed June 27,1990 U.S. patent application Ser. No. 07/544,765, for AN ELUANT AND PREPARATION APPARATUS AND METHOD FOR USING THE SAME, filed June 27, 1990 and U.S. patent application Ser. No. 07/544,768, for ZERO GRAVITY COMPATIBLE TOTAL ORGANIC AND INORGANIC CARBON ANALYZER, filed June 27, 1990, all commonly assigned.

TECHNICAL FIELD

The present invention relates to a purge and trap technique, and especially to a zero gravity compatible purge and trap technique for monitoring volatile organic compounds.

BACKGROUND ART

The types and amount of contaminants in water, especially potable water, are often monitored to ensure the water can safely be consumed. Since a large number of volatile organic compounds are toxic and carcinogenic, they are among the compounds often monitored. Traditionally, volatile organic compounds are monitored using a purge and trap technique. This method is required by the United States Environmental Protection Agency for monitoring many of the regulated hazardous substances in water.

The purge and trap technique consists of placing a water sample in a gas tight vessel and contacting this sample with an inert gas. The inert gas purge extracts the volatile organic compounds from the aqueous phase into the gaseous phase. The inert gas with the volatile organic compounds is then passed over an adsorbent which traps the volatile organic compounds, thereby allowing the purge gas to be separated from the volatile organic compounds. This process, although effective, is not capable of operating in zero gravity environment (hereafter referred to as zero gravity compatible). The liquid and gas phases are not readily separated due to the lack of gravity.

What is needed in the art is a technique for purge and trap sample preparation for volatile organic compounds in an aqueous sample which can be automated and can function in a zero gravity environment.

DISCLOSURE OF INVENTION

The present invention comprises a zero gravity purge and trap sample preparation apparatus and a process which can be used to analyze volatile organic compounds. The apparatus is comprised of a gas tight containment vessel, a microporous hydrophobic bladder, a means for separating volatile organic compounds, a means for heating, and a means for analyzing volatile organic compounds.

Utilization of the present invention comprises placing an aqueous sample into the collapsed microporous hydrophobic bladder within the containment vessel. An inert gas is introduced to the microporous hydrophobic bladder as a purge, causing the volatile organic compounds to enter the gas phase. Once in the gas phase, both the inert and volatile organic gases permeate the microporous hydrophobic bladder membrane, moving into the void between the microporous hydrophobic bladder and the containment vessel. The inert gas then sweeps the volatile organic compounds into the means for separating volatile organic compounds. After a sufficient amount of volatile organic compounds has been adsorbed, heat is added to the means for separating volatile organic compounds, causing desorption of the volatile organic compounds which are then analyzed.

The foregoing and other features and advantages of the present invention will become more apparent from the following description and accompanying drawing.

BRIEF DESCRIPTION OF DRAWINGS

The FIGURE is a schematic of one possible embodiment of the zero gravity purge and trap volatile organic compound analyzer of the present invention.

BEST MODE FOR CARRYING OUT THE INVENTION

Referring to the FIGURE, which is meant to be exemplary not limiting, the system of the present invention utilizes a means for metering the sample (20), a containment vessel (30), an inert gas supply (40), a means for separating volatile organic compounds (50), means for heating (60), and a means for analyzing volatile organic compounds (70). The containment vessel, which is gas tight, is comprised of a sample inlet (10), a sample outlet (80), a microporous hydrophobic bladder (32), an inert gas purge inlet (36), and a vent (34).

An aqueous sample is supplied through inlet (10) into the microporous hydrophobic bladder (32) within the containment vessel (30). Inert gas is bubbled through (hereafter referred to as purged) the aqueous sample, causing the volatile organic compounds to enter the vapor phase and permeate the microporous hydrophobic bladder (32) membrane. The volatile organic compounds are then swept to the means for separating volatile organic compounds (50). In the means for separating volatile organic compounds (50), the volatile organic compounds are adsorbed while the inert carrier gas is vented. The means for separating volatile organic compounds (50) is then heated to desorb the volatile organic compounds. These volatile organic compounds are then routed to the means for analyzing volatile organic compounds (70) for analysis. The spent aqueous sample in the containment vessel (30) can be removed to a dump or sample reclamation (80).

Any means known in the art, such as standard metering pumps and micrometering pumps can be used to transport an aqueous sample into the microporous hydrophobic bladder (32). Generally the means for metering only transports small volumes at low rates, for example up to about 10 milliliters (ml) per minute.

The microporous hydrophobic bladder (32) is located within the gas containment vessel (30). The bladder is preferably a microporous hydrophobic bladder which allows the separation of the volatile organic compounds from the aqueous sample through permeation of the bladder membrane. The microporous hydrophobic bladder should have a pore size in the range of about 0.20 microns to about 2.0 microns, with about 0.20 microns preferred for monitoring volatile organic compounds. Note, it is recognized that if this process is used to monitor a different aqueous solution contaminant, a different pore size may be necessary. The microporous hydrophobic bladder (32) can be composed of any substance which is hydrophobic and which does not interfere with the passage of the volatile organic compounds. Various types of possible microporous hydrophobic bladders include Goretex, produced by W. L. Gore & Associates, Elkton, Md., or any other open cell hydrophobic materials exhibiting hydrophobic/gas permeation and water retention characteristics. Note, the microporous hydrophobic bladder is initially fully collapsed to prevent voids which can interfere with the liberation of the volatile organic compounds and the overall analysis. The bladder expands as the aqueous sample and the inert gas enter and collapses again as the aqueous sample, inert gas, and volatile organic compounds exit; preventing voids.

The containment vessel (30) encompasses the microporous hydrophobic bladder (32) leaving a void between the microporous hydrophobic bladder membrane and the inner wall of the containment vessel; the bladder is smaller than the inner diameter of the containment vessel. This enables the volatile organics to readily pass through the microporous hydrophobic bladder (32) into the void space. The containment vessel (30) should be between about 10% and about 50% larger than the microporous hydrophobic bladder (32) in order to ensure free flow of the volatile organic compounds. Note, a larger containment vessel can be used. The containment vessel can be composed of any substance which is not degraded by and does not react with the volatile organic compounds, and is gas tight. Metallics are preferred because the sample will not permeate metallics and metallics will not contribute organic contaminants to the sample.

Once the aqueous sample is in the microporous hydrophobic bladder (32), the volatile organic compounds are liberated from the liquid phase by an inert gas purge. The purge causes the volatile organic compounds to enter the vapor phase. The amount of time to remove the volatile organic compounds from the aqueous sample to the vapor phase via an inert gas purge is dependant upon the types of volatile organics, size of the aqueous sample, and the flow rate of the inert gas. The time period, which can be easily determined by one skilled in the art, should be sufficient to transport the majority of the volatile organic compounds from the aqueous sample to the vapor phase. Typically, the time period ranges from about 3.0 minutes (min.) to about 30.0 min.

Once in the vapor phase, the volatile organic compounds and the inert gas permeate the microporous hydrophobic bladder (32) membrane. The inert gas then acts as a carrier gas, sweeping the vaporized volatile organic compounds into the means for separating volatile organic compounds (50) which adsorbs the volatile organic compounds are adsorbed. Any inert gas which does not react with any part of the system can be utilized. Preferred inert gases include, argon, helium, and nitrogen, with nitrogen preferred for reasons of availability and cost.

The adsorption of the volatile organic compounds is accomplished by intimate contact with a sorbent bed within the means for separating volatile organic compounds (50). By adsorbing the volatile organic compounds, the means for separating volatile organic compounds separates the volatile organic compounds from the inert gas and any water vapor, preparing the volatile organic compounds for analysis. The means for separating volatile organic compounds can be any means conventionally known in the art capable of separating volatile organic compounds from inert gas, such as a sorbent trap which adsorbs the vaporized volatile organic compounds. Various types of means for separating volatile organic compounds can be used, such as carbon or organic polymer based means for separating volatile organic compounds, including Tenax/charcoal trap, the Tenax trap, and the Tenax/charcoal/silica trap, all of which are produced by Tekmar Co., Cincinnati, Oh. The Tenax/charcoal trap is preferred for reasons of high organic capacity (higher capacity for volatile organic compounds than other charcoal or polymeric sorbents known in the art), wide range of adsorption, and minimal degradation due to repeated heat cycling.

After the separation from the inert gas is complete, the volatile organic compounds are liberated. Liberation is a desorption process accomplished by applying heat to the means for separating volatile organic compounds (50)' any desorption method conventionally known in the art can be used. The means for separating volatile organic compounds (50) is heated to temperatures sufficient to desorb the volatile organic compounds. This temperature can easily be determined by an artisan. Factors which effect the desorption temperature include the specific type of means for separating volatile organic compounds, the type of volatile organic compounds, the volume of the organic compounds. For example, for a Tenax/charcoal trap, desorption temperatures typically range between about 300° F. and about 390° F., temperatures exceeding 450° F. can cause sorbent trap degradation. The means for heating the means for separating volatile organic compounds can be any means conventionally known in the art capable of zero gravity heating application, including in line heat exchangers, forced convection, and heating tapes.

It is preferred that at least 80% of the volatile organic compounds be adsorbed by the means for separating volatile organic compounds (50) prior to liberation. It is especially preferred that greater than 95% of the volatile organic compounds be adsorbed. The amount of volatile organic compounds adsorbed can be determined by standard recovery practices.

The flow rate of the volatile organic compounds and the inert gas through the means for separating volatile organic compounds (50) is dependent upon the type of means for separating volatile organic compounds utilized, the types of volatile organic compounds, the sample size, the concentration of the volatile organic compounds, the system volume desired, and the percent recovery desired. For example, when a 2 cc Tenax/charcoal trap is utilized, the flow rate is between about 30.0 ml/min. and about 50 ml/min., with 40 ml/min. preferred due to adsorption efficiency.

The liberated volatile organic compounds are analyzed in a means for analyzing volatile organic compounds. The means for analyzing volatile organic compounds (70) can be any means capable of determining the types and concentration of volatile organic compounds present, such as gas chromatograph (GC) and gas chromatograph/mass spectrometer (GC/MS).

EXAMPLE

The following example can be used to separate volatile organic compounds from a water sample so that the concentrations of various volatile organic compounds can be determined to establish the potability of the water.

1. 5.0 ml of water is metered at a flow rate of 5.0 ml/min. into the microporous hydrophobic bladder having a pore size of 0.2 microns.
2. The water is purged with nitrogen at a rate of 40 ml/min. for 11.0 min., with the goal of achieving at least 80% recovery of the volatile organic compounds of interest. The volatile organic compounds enter the vapor phase and pass to the outside of the microporous hydrophobic bladder within the containment vessel.
3. The vaporized volatile organic compounds are carried to the 2 cc Tenax/charcoal trap via the inert gas, nitrogen, which passes through the microporous hydrophobic bladder at a rate of 40 ml/min. for 11.0 minutes.
4. The trap is heated to 356° F. to desorb the volatile organic compounds which are carried to a GC/MS analyzer via the inert purge gas.
5. The liberated volatile organic compounds are then analyzed with a GC/MS.

Prior art purge and trap devices are not zero gravity compatible. The traditional purge and trap approach, in a zero gravity environment, would force the aqueous sample out of the purge vessel. Furthermore, no means for gas/liquid phase separation exists with current configuration purge and trap devices. This invention uses a microporous hydrophobic bladder material which is not permeable to aqueous solutions but is permeable to gases and the volatile organic compounds of interest. The microporous hydrophobic bladder effectively separates the aqueous phase from the inert gas and the volatile organic compounds. Additionally, since the inert gas and volatile organic compounds pass through the membrane, a phase separator is not necessary in the down stream liquid line. Also, not only is the present invention zero gravity compatible, it is automatable.

Although this invention has been shown and described with respect to detailed embodiments thereof, it will be understood by those skilled in the art that various changes in form and detail thereof may be made without departing from the spirit and scope of the claimed invention.

We claim:

1. An apparatus for zero gravity purge and trap sample preparation for separating volatile organic compounds from an aqueous sample and for analyzing said volatile organic compounds, which comprises:
   a. a gas tight containment vessel containing a microporous hydrophobic bladder;
   b. a means for introducing the aqueous sample to said microporous hydrophobic bladder;
   c. a means for introducing an inert, volatile organic compound liberating gas purge to said aqueous sample;
   d. a means for separating volatile organic compounds;
   e. a means for introducing volatile organic compounds; and
   f. a means for analyzing;
   wherein said means for introducing an inert gas purge is in flow communication with said means for introducing the aqueous sample and said bladder, said means for introducing the inert gas purge liberating any volatile organic compounds from said aqueous sample;
   wherein said means for separating volatile organic compounds in flow communication with said bladder, said means for separating volatile organic compounds constructed so as to separate the volatile organic compounds from said inert gas;
   wherein said means for separating said volatile organic compounds in flow communication with said means for analyzing.

2. An apparatus as in claim 1 wherein the microporous hydrophobic bladder has a pore size between about 0.20 microns and about 2.0 microns.

3. An apparatus as in claim 1 wherein the means for separating said volatile organic compounds as is a sorbent trap.

4. An apparatus as in claim 3 wherein said sorbent trap comprises a sorbent selected from the group consisting of carbon based compounds, organic polymer based compounds, and mixtures thereof.

5. An apparatus as in claim 1 wherein said means for analyzing volatile organic compounds is selected from the group consisting of a gas chromatograph and a gas chromatograph/mass spectrometer.

6. A process for analyzing volatile organic compounds in an aqueous sample which is zero gravity compatible, which comprises:
   a. placing the aqueous sample into a microporous hydrophobic bladder located within a containment vessel, wherein the microporous hydrophobic bladder has a membrane;
   b. purging the aqueous sample with an inert gas to remove volatile organic compounds from the aqueous sample;
   c. causing the volatile organic compounds and inert gas to permeate the microporous hydrophobic bladder membrane;
   d. separating the volatile organic compounds from the inert gas in a means for separating volatile organic compounds; and
   e. analyzing the volatile organic compounds wherein said process determines the quantity of volatile organic compounds present in said aqueous sample.

7. A process as in claim 6 wherein the pore size of said microporous hydrophobic bladder is between about 0.20 microns and about 2.0 microns.

8. A process as in claim 6 wherein the inert gas is selected from the group consisting of argon, helium, and nitrogen.

9. A process as in claim 6 wherein the means for separating volatile organic compounds is a sorbent trap.

10. A process as in claim 9 wherein the sorbent trap is selected from the group consisting of carbon based and organic polymer based.

11. A process as in claim 6 wherein the step of analyzing the volatile organic compounds comprises employing an analyzer selected from the group consisting of a gas chromatograph and a gas chromatograph/mass spectrometer.

12. A process as in claim 6 wherein the bladder comprises a flexible collapsible and expandable bladder and wherein the step of placing said aqueous sample into the flexible bladder expands said bladder to a volume commensurate with the volume of aqueous sample and inert gas occupying said bladder.

* * * * *